United States Patent [19]

Numazawa et al.

[11] Patent Number: 5,207,946

[45] Date of Patent: May 4, 1993

[54] LIQUID CRYSTAL COMPOUNDS

[75] Inventors: Koichi Numazawa; Noriko Yamakawa; Yoshiichi Suzuki; Ichiro Kawamura, all of Tokyo, Japan

[73] Assignee: Showa Shell Sekiyu K.K., Tokyo, Japan

[21] Appl. No.: 557,845

[22] Filed: Jul. 25, 1990

[30] Foreign Application Priority Data

Jul. 26, 1989 [JP] Japan .................................. 1-193694

[51] Int. Cl.$^5$ ...................... C09K 19/12; C09K 19/20; C07C 69/76
[52] U.S. Cl. .......................... 252/299.65; 252/299.66; 252/299.67; 560/59; 560/60; 560/65; 560/102; 560/111
[58] Field of Search ...................... 252/299.67, 299.66, 252/299.65; 560/59, 60, 65, 102, 111

[56] References Cited

U.S. PATENT DOCUMENTS

| | | | |
|---|---|---|---|
| 4,917,817 | 4/1990 | Nohira et al. | 252/299.01 |
| 4,918,213 | 4/1990 | Nohira | 588/271 |
| 4,921,632 | 5/1990 | Nakamura et al. | 252/299.1 |
| 4,973,738 | 11/1990 | Suzuki et al. | 560/80 |

FOREIGN PATENT DOCUMENTS

| | | | |
|---|---|---|---|
| 21181238 | 8/1987 | Japan | 560/102 |
| 2-040346 | 2/1990 | Japan | 560/59 |
| 2-045450 | 2/1990 | Japan | 560/102 |
| 8707890 | 12/1987 | World Int. Prop. O. | |

OTHER PUBLICATIONS

Liquid Crystals, vol. 6, No. 2, Aug. 1989, pp. 167–174, Taylor & Francis, London, GB: Y. Suzuki et al.: New Fluorine-Containing Ferroelectric Liquid Crystal Compounds Showing Tristable Switching.
Patent Abstracts of Japan, vol. 13, No. 151 (C-584[3499], Apr. 12, 1989, p. 26 C584; and JP-A-63 307 837 (Daicel Chem. Inc. Ltd) Dec. 15, 1988.
A. D. L. Chandani et al., Tristable Switching in Surface Stablized Ferroelectric Liquid Crystals with a Large Spontaneous Polarization, Japanese Journal of Applied Physics, vol. 27, No. 5, May, 1988, pp. L729–L732.
Masahiro Johno et al., Temporal and Spatial Behavior of the Field-Induced Transition Between Antiferroelectric and Ferroelectric Phases in Chiral Smectics, Japanese Journal of Applied Physics, vol. 29, No. 1, Jan., 1990, pp. L107–L110.
Hiroshi Orihara, Experimental Studies on Phase Transitions in an Antiferroelectric Liquid Crystal Japanese Journal of Applied Physics, vol. 29, No. 2, Feb. 1990, pp. L333–L335.

*Primary Examiner*—Robert L. Stoll
*Assistant Examiner*—C. Harris
*Attorney, Agent, or Firm*—Sughrue, Mion, Zinn, Macpeak & Seas

[57] ABSTRACT

A liquid crystal compound represented by formula (I):

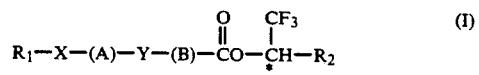

wherein $R_1$ represents an alkyl group having from 3 to 18 carbon atoms; $R_2$ represents an alkyl group having from 3 to 18 carbon atoms; X represents

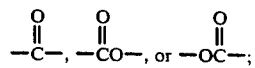

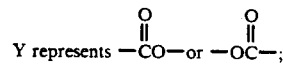

(A) and (B) each represents a group selected from the group consisting of

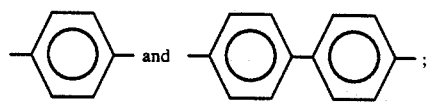

and * indicates an optically active center.

3 Claims, 5 Drawing Sheets

TRIANGULAR WAVE APPLIED

ELECTRO-OPTIC RESPONSE OF COMMERCIAL NEMATIC LIQUID CRYSTAL

ELECTRO-OPTIC RESPONSE OF CONVENTIONAL BISTABLE LIQUID CRYSTAL

ELECTRO-OPTIC RESPONSE OF TRISTABLE LIQUID CRYSTAL OF INVENTION

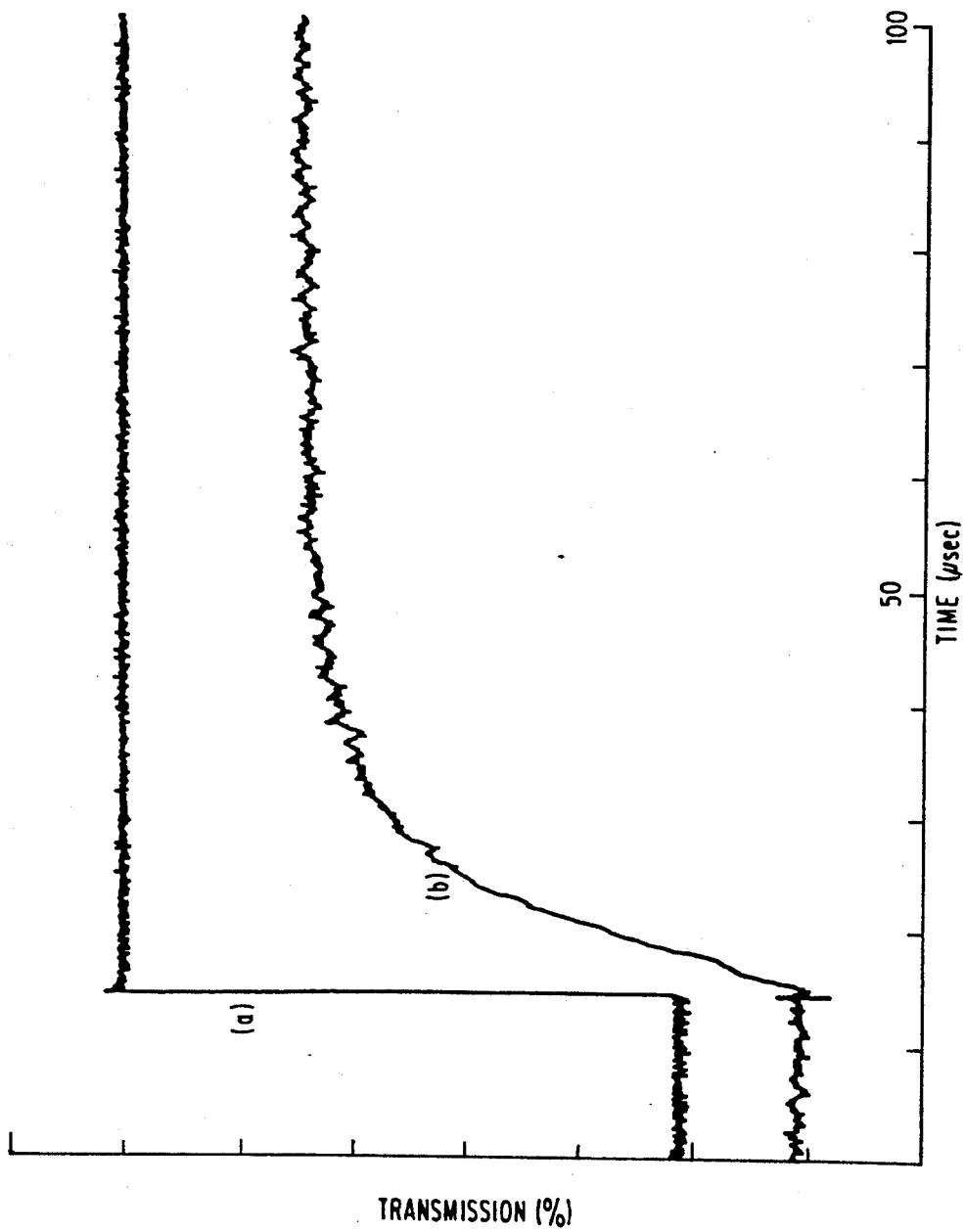

LIQUID CRYSTAL COMPOUNDS

FIELD OF THE INVENTION

This invention relates to ferroelectric chiral smectic liquid crystal compounds which are suitable for use in electro-optical display devices. This invention also relates to ferroelectric liquid crystal compounds exhibiting three stable molecular orientation states which are suitable for use in display elements or electro-optic elements utilizing a response to an electric field.

BACKGROUND OF THE INVENTION

Electro-optic devices using liquid crystals which have hitherto been developed and put into practical use include those using nematic liquid crystals, such as a DSM mode, a TN mode, a G-H mode, and an STN mode. However, any of these devices using nematic liquid crystals has a very slow electro-optic response requiring a switching time from several to several tens milliseconds and is hence limited in range of application. The slow response of the elements using nematic liquid crystals is because the torque of moving molecules, basically being based on anisotropy of dielectric constant, is not so strong. Under such circumstances, Meyer, et al. developed ferroelectric liquid crystals which undergo spontaneous polarization (Ps) and has a strong torque, the torque being based on Ps x E (applied electric field), and thereby has a high-speed response in the order of microseconds as disclosed in Le Journal de Physique, Vol. 36, L 69 (1975). Further, JP-A-63-307837 (the term "JP-A" as used herein means an "unexamined published Japanese patent application") discloses new ferroelectric liquid crystals, but gives no description about "three states" hereinafter described.

Several high-speed electro-optic devices using ferroelectric liquid crystals have already been proposed. Typically included in such devices is an element in which a twisted structure is untwisted by the force of a wall surfaces, and two molecular alignment layers in parallel in the wall surface are varied by polarity of the applied electric field as described, e.g., in JP-A-56-107216.

Existence of a compound showing ideal two states having an electric field response waveform as shown in FIG. 1 is prerequisite to realization of the above-described device. However, such a compound exhibiting ideal two states has not yet been discovered. Any of the so far synthesized bistable liquid crystals has a response waveform as shown in FIG. 2 but not that of FIG. 1. When the state-of-the-art liquid crystals having a response waveform of FIG. 2 are used, for example, in light switching circuits, since a transmission gradually changes according as an applied voltage changes from negative to positive, the purpose cannot be sufficiently accomplished simply by changing the applied voltage between "on" and "off". Moreover, so far synthesized bistable liquid crystals find difficulty in making a monodomain state in its Sc* phase with no voltage applied, i.e., an ideal molecular orientation state, easily causing defect or a molecular orientation disturbance called twist. Thus, it has been difficult to realize the above-stated ideal two states of molecular orientation over a wide area. Further, because the threshold value (voltage at which a luminance changes by a prescribed value) is low, dynamic driving is liable to suffer from reduction in contrast or reduction in viewing angle. Furthermore, these conventional bistable liquid crystals do not exhibit hysteresis as shown in FIG. 1 but that shown in FIG. 2 so that they have no memory effect. Therefore, it is necessary to continue applying a voltage of $v_3$ of FIG. 2 or applying a high frequency for the liquid crystal to maintain a stable response in the Sc* phase, which, in either case, entails a considerable energy loss.

Thus, the conventional electro-optic devices have many problems waiting for solution notwithstanding the strong demand for making effective use of the strong connection between an applied electric field and molecular orientation exhibited by ferroelectric liquid crystals.

SUMMARY OF THE INVENTION

An object of this invention is to provide a novel liquid crystal compound which exhibits a stable molecular orientation state having a high light/shade contrast with no electric field applied, has clear threshold characteristics and clear hysteresis as shown in FIG. 3, easily realizes dynamic driving, and is applicable to liquid crystal electro-optic devices utilizing three states which make it possible to obtain a high-speed response.

More specifically, an object of this invention is to provide a novel ferroelectric liquid crystal exhibiting a chiral smectic (Sc*) phase.

Another object of this invention is to provide a novel ferroelectric liquid crystal exhibiting three states which are entirely different from a chiral semctic C phase (Sc* phase), a conventional bistable state phase.

The terminology "three states" as used herein means three stable states of molecular orientation explained below. In a liquid crystal electro-optic device comprising a pair of electrode substrates with a prescribed gap therebetween and a ferroelectric liquid crystal being sandwiched between the pair of substrates, the electrodes being connected to an electric power source so that a voltage of triangular wave as shown in FIG. 4 (A) is applied, the ferroelectric liquid crystal shows a first stable state of molecular orientation as shown by numeral 2 of FIG. 4(D) with no electric field applied, a second stable state of molecular orientation as shown by numeral 1 of FIG. 4(D) differing from the first stable state with an electric field applied to one direction, and a third stable state of molecular orientation as shown by numeral 3 of FIG. 4(D) differing from either of the first and second stable states with an electric field applied to another direction. With respect to liquid crystal electro-optic devices utilizing these three stable states, the inventors have already filed a Japanese patent application No. 70212/88.

To the contrary, commercially available nematic liquid crystals and so far synthesized bistable liquid crystals have no such three stable states as revealed in FIGS. 4(B) and (C), respectively.

The above-stated ferroelectric liquid crystals having three states (hereinafter sometimes referred to as tristable liquid crystals) according to the present invention produce striking effects when applied to liquid crystal displays as compared with the conventional nematic liquid crystals as follows.

While the conventional liquid crystals should be driven through a very complicated system called an active matrix system, the tristable ferroelectric liquid crystal can be driven through a simple matrix display. Accordingly, the display element using the tristable ferroelectric liquid crystal can be produced by easy steps and makes it feasible to widen the display area and to reduce the production cost, whereas the conventional display elements require complicated production steps, encounter difficulty in widening the display area, and incur high production cost.

That is, the present invention provides a liquid crystal compound represented by formula (I):

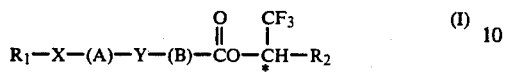

wherein $R_1$ represents an alkyl group having from 3 to 18 carbon atoms; $R_2$ represents an alkyl group having from 3 to 18 carbon atoms; X represents

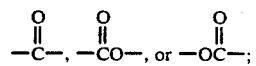

Y represents 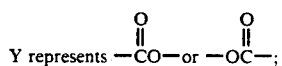

(A) and (B) each represents a group selected from the group consisting of

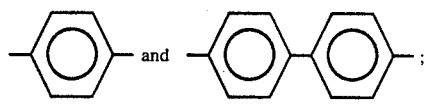

and * indicates an optically active center.

The present invention also provides a liquid crystal compound represented by formula (I), wherein $R_1$ represents an alkyl group having from 5 to 18 carbon atoms; $R_2$ represents an alkyl group having from 4 to 15 carbon, which exhibits three stable states.

BRIEF DESCRIPTION OF THE DRAWINGS

FIG. 5 shows an electro-clinic effect, in which (a) is an alternating voltage applied to a liquid crystal electro-optic element, and (b) shows changes of transmission with the alternating voltage (a).

DETAILED DESCRIPTION OF THE INVENTION

Figure 1:
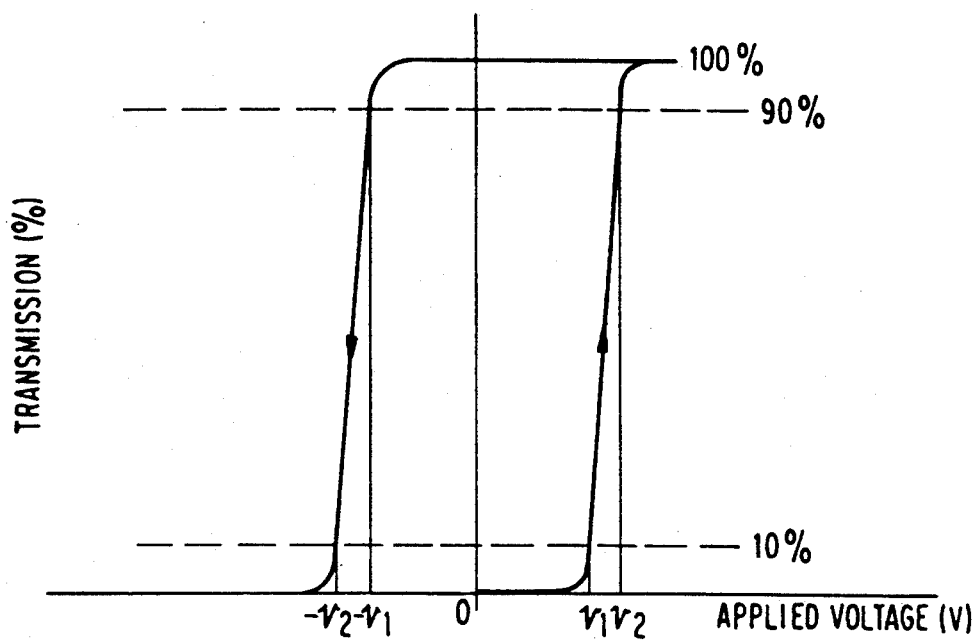
FIG. 1, 2, and 3 each shows hysteresis of an ideal bistable liquid crystal which is not actually available, a conventional crystal which is not actually available, a conventionally developed bistable liquid crystal, and a tristable liquid crystal according to the present invention, respectively, in which an applied voltage is plotted as abscissa and a transmission (%) as ordinate.
Figure 2:
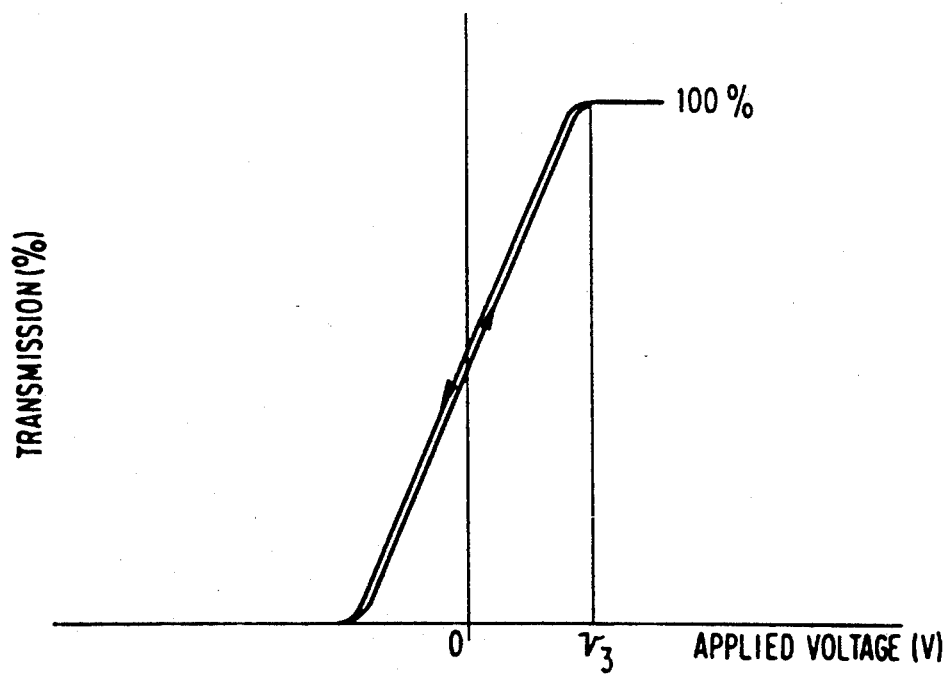
Figure 3:
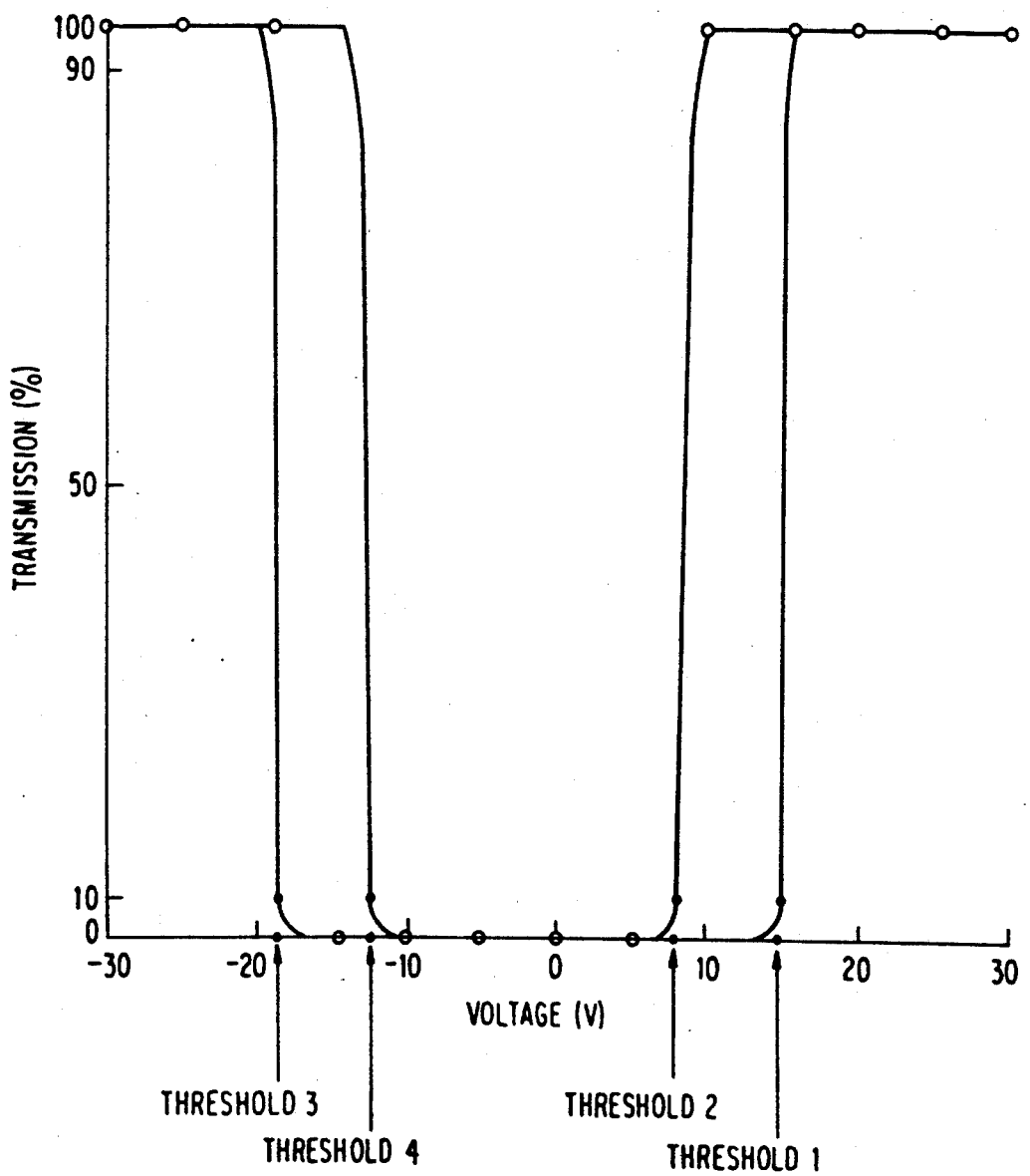
Figure 4A:
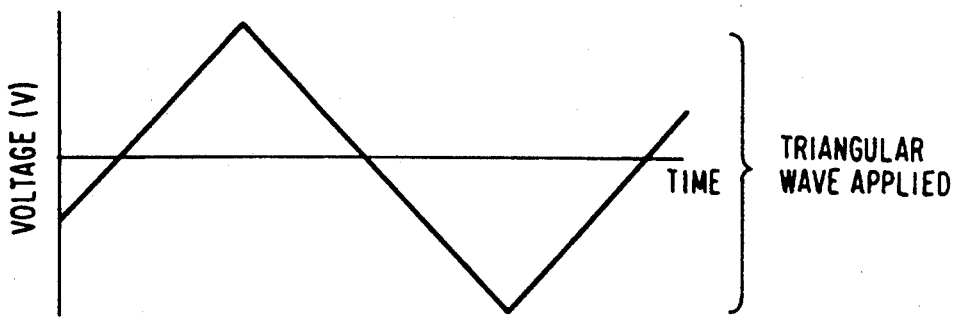
FIG. 4(A) shows a triangular wave applied.
Figure 4B:
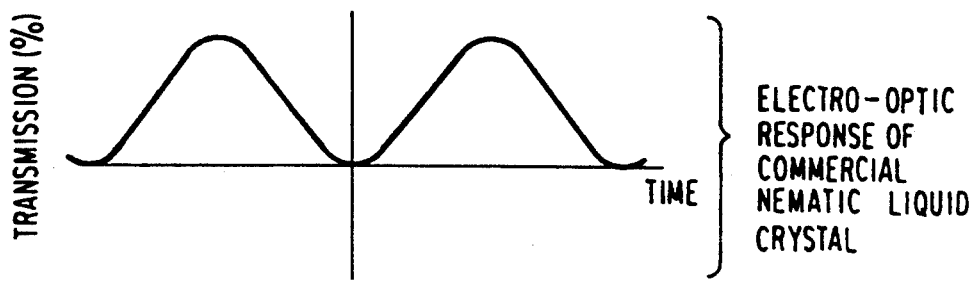
FIGS. 4(B), (C), and (D) each shows an electro-optic response of a commercially available nematic liquid crystal, a conventionally synthesized bistable liquid crystal, and a tristable liquid crystal according to the present invention, respectively.
Figure 4C:
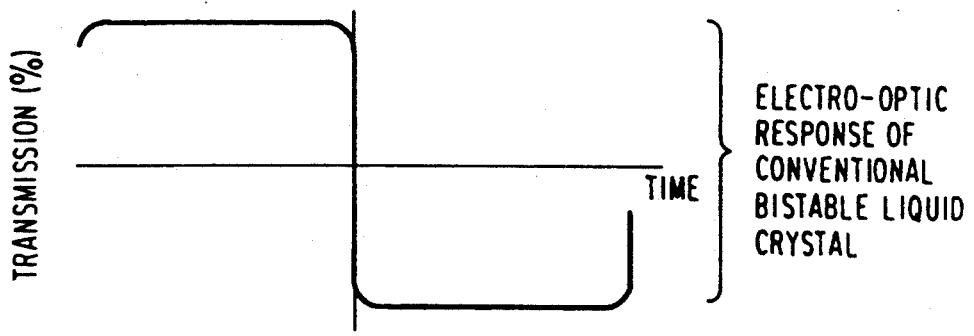
Figure 4D:
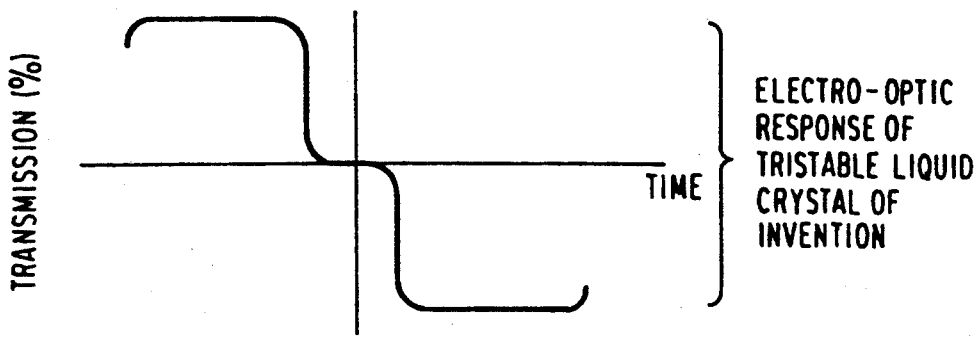

Specific examples of preferred compounds represented by formula (I) are shown below.

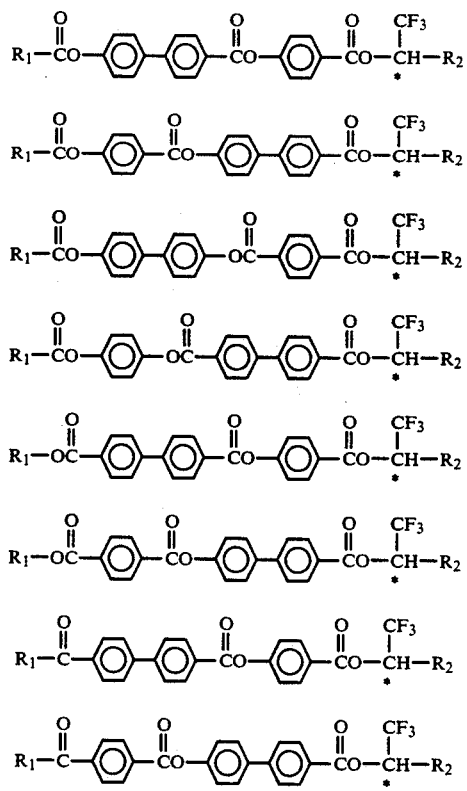

wherein $R_1$ and $R_2$ are as defined above.

In formula (I) and the above-illustrated formulae, $R_1$ preferably represents an alkyl group having from 5 to 18 carbon atoms, and more preferably a straight chain alkyl group having from 6 to 12 carbon atoms. $R_2$ preferably represents an alkyl group having from 4 to 15 carbon atoms, and more preferably a straight chain alkyl group having from 5 to 12 carbon atoms.

Synthesis examples of the compounds according to the present invention are shown below.

SYNTHESIS EXAMPLE 1

4-Benzyloxybenzoic acid chloride and an optically active 1,1,1-trifluoro-2-alkanol were reacted to obtain a -benzyloxybenzoic acid 1,1,1-trifluoro-2-alkyl ester. The ester was hydrogenated to obtain a 4-hydroxybenzoic acid 1,1,1-trifluoro-2-alkyl ester. The resulting alkyl ester was then reacted with a 4-n-alkanoyloxyphenyl(or biphenyl)carboxylic acid chloride to obtain a desired compound, an optically active 4-(1,1,1-trifluoro-2-alkyloxycarbonyl)phenyl 4-n-alkanoyloxybenzoate (or biphenylcarboxylate).

SYNTHESIS EXAMPLE 2

Terephthalic acid chloride was reacted with an optically active 1,1,1-trifluoro-2-alkanol to obtain a terephalic acid 1,1,1-trifluoroalkyl monoester, which was then reacted with a 4-alkanoyloxy-4'-hydroxybiphenyl to obtain an optically active 4-alkanoyloxybiphenyl 4-(1,1,1-trifluoro-2-alkyloxycarbonyl)benzoate.

The present invention is now illustrated in greater detail by way of Examples, but it should be understood that the present invention is not deemed to be limited thereto. In Examples, phase transition points of liquid crystals were measured by means of DSC (differential scanning calorimeter) combined with microscopic observation on hot stage.

EXAMPLE 1

(1) Synthesis of 1,1,1-Trifluoro-2-decyl 4-Benzyloxybenzoate:

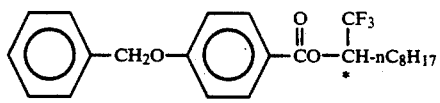

In 10 ml of methylene chloride was dissolved 1.23 g of 4-benzyloxybenzoic acid chloride, and a solution of 0.96 g of optically active 1,1,1-trifluoro-2-decanol, 0.55 g of dimethylaminopyridine, and 0.48 g of triethylamine in ml of methylene chloride was added thereto in small portions under ice-cooling.

The reaction mixture was allowed to warm to room temperature and was reacted at that temperature for one day. The reaction mixture was poured into ice-water and extracted with methylene chloride. The methylene chloride phase was washed successively with diluted hydrochloric acid, water, a 1N sodium carbonate aqueous solution, and water and dried over anhydrous magnesium sulfate. The solvent was removed by distillation to obtain a crude product. The crude product was purified by column chromatography using silica gel and toluene and then recrystallization from ethanol to obtain 1.84 g of the entitled compound.

(2) Synthesis of 1,1,1-Trifluoro-2-decyl 4-Hydroxybenzoate:

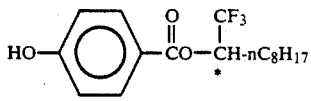

The Compound obtained in 1) above was dissolved in 15 ml of ethanol, and 0.36 g of 10% palladium-on-carbon was added to solution to conduct hydrogenation in a hydrogen atmosphere to obtain 1.43 g of the entitled compound.

(3) Synthesis of 4-(1,1,1-Trifluoro-2-decyloxycarbonyl)phenyl 4'-n-Nonanoyloxybiphenyl-4-carboxylate:

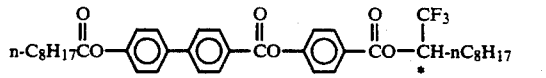

4'-n-Nonanoyloxybiphenyl-4-carboxylic acid (1.20 g) was refluxed together with an excess of thionyl chloride for 6 hours. The unreacted thionyl chloride was removed by distillation to obtain 4'-n-nonanoyloxydiphenylcarboxylic acid chloride.

The resulting acid chloride was dissolved in 12.0 ml of methylene chloride, and a solution of 1.00 g of the above-prepared 1,1,1-trifluorodecyl ester, 0.32 g of triethylamine, and 0.37 g of dimethylaminopyridine in 30 ml of methylene chloride was slowly added thereto under ice-cooling, and the mixture was allowed to react at room temperature for one day.

The reaction mixture was poured into ice-water and extracted with methylene chloride. The extract was washed successively with diluted hydrochloric acid, water, a sodium carbonate aqueous solution, and water and dried over anhydrous sodium sulfate. The solvent was removed by distillation to obtain a crude product. The crude product was purifued by column chromatography using silica gel and toluene to obtain 1.1 g of the desired optically active compound.

Phase transition points of the resulting compound were determined after recrystallization from absolute ethanol.

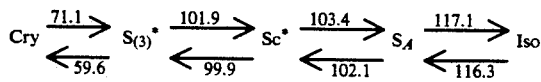

EXAMPLE 2

Synthesis of 4-n-(1,1,1-Trifluoro-2-octyloxy-carbonyl) phenyl 4'-n-Nonanoyloxybiphenyl-4-carboxylate

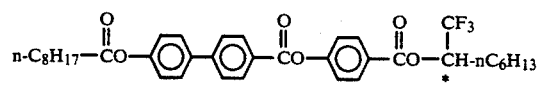

The entitled optically active compound was synthesized in the same manner as in Example 1, except for replacing 1,1,1-trifluoro-2-decanol as used in (1) of Example 1 with 1,1,1-trifluoro-2-octanol.

Phase transition temperature of the resulting compound was determined by DSC and microscopic measurements.

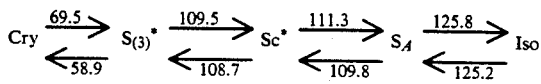

EXAMPLE 3

Synthesis of 4-n-(1,1,1-Trifluoro-2-octyloxycarbonyl)-phenyl 4-'-n-Decyloxycarbonylbiphenyl-4-carboxylate

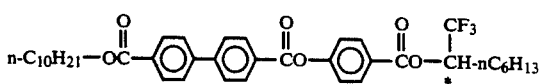

The entitled optically active compound was synthesized in the same manner as in Example 1, except for replacing 4'-nonanoyloxybiphenyl-4-carboxylic acid as used in 3) of Example 1 with 4'-decyloxycarbonylbiphenyl-4-carboxylic acid.

Phase transition temperature of the resulting compound was determined by DSC and microscopic measurements.

EXAMPLE 4

Synthesis of 4'-n-Undecanoyloxybiphenyl-4-(1,1,1-Trifluoro-2-octyloxycarbonyl)benzoate

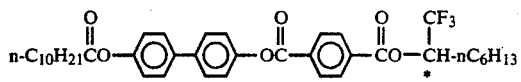

(1) Synthesis of 1,1,1-Trifluoro-2-octylterephthalic Monoester:

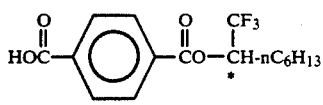

In 50 ml of methylene chloride was dissolved 11.2 g of terephthalic acid chloride, and 10.0 g of optically active 1,1,1-trifluoro-2-octanol and 13 g of pyridine were added dropwise to the solution under ice-cooling. The reaction mixture was allowed to warm to room temperature, and the reaction was continued at that temperature for one day. The reaction mixture was washed successively with diluted hydochloric acid, water, a 1N sodium bicarbonate aqueous solution, and water. The organic layer collected was dried over anhydrous magnesium sulfate, and the solvent was removed by distillation under reduced pressure. The resulting crude product was purified by column chromatography using silica gel and toluene and then recrystallization from ethanol to obtain 3.3 g of the entitled compound.

(2) Synthesis of 4'-n-Undecanoyloxybiphenyl-(4) 4-(1,1,1-Trifluoro-2-octyloxycarbonyl)benzoate:

To 100 ml of a tetrahydrofuran solvent were added 3.3 g of the 1,1,1-trifluoro-2-octylterephthalic acid monoester obtained in 1) above, 3.5 g of 4-undecanoyloxy4'-hydroxybiphenyl, 3.19 g of dicyclohexylcarbodiimide, and 0.3 g of dimethylaminopyridine, and the mixture was allowed to react at room temperature for one day.

After the tetrahydrofuran solvent in the reaction mixture was appropriately reduced by vacuum distillation, the mixture was poured into cool water and extracted with methylene chloride. The extract was thoroughly washed successively with an aqueous 1N sodium bicarbonate solution, water, diluted hydrochloric acid, and water until the washing became neutral and dried over anhydrous sodium sulfate. The solvent was removed by distillation, and the resulting crude product was purified by column chromatography using silica gel and toluene and then repeated recrystallization from ethanol to obtain 1.5 g of an optically active desired compound.

$[\alpha]_D^{20} = +23.8°$

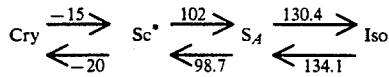

EXAMPLE 5

Synthesis of 4-n-Decyloxycarbonylphenyl 4'-(1,1,1-Trifluoro-2-octyloxycarbonyl)biphenyl-4-carboxylate

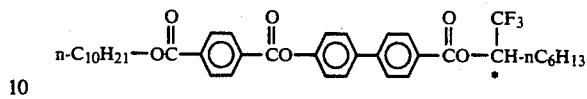

4-(1,1,1-Trifluoro-2-octyloxycarbonyl)biphenyl-4-carboxylate

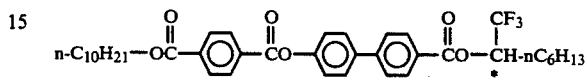

4-(1,1,1-Trifluoro-2-octyloxycarbonyl)-4'-hydroxybiphenyl (0.5 g) and 0.4 g of n-4-decyloxycarbonylbenzoic acid were reacted in 30 ml of tetrahydrofuran in the presence of 0.3 g of dicyclocarbodiimide and a few pieces of dimethylaminopyridine. The resulting crude product was purified by silica gel column chromatography using a 10:0.5 (by volume) mixture of hexane and ethyl acetate as an eluent and then recrystallization from ethanol to obtain 0.1 g of the entitled optically active compound.

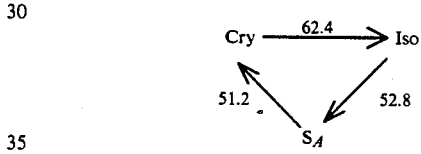

EXAMPLE 6

The liquid crystal compound obtained in Example 1 was filled while in an isotropic phase into a liquid crystal cell having a polyimide orientation film having been subjected to a rubbing treatment on an ITO (indium tin oxide) electrode substrate (cell thickness: 2.9 μm).

The resulting cell was slowly cooled at a rate of 0.1° to 1.0° C./min to orientate the liquid crystal molecules in an $S_A$ phase. A square wave voltage of ±30V and 10 Hz was applied, and an electro-optic response was detected with a polarizing microscope equipped with a photomultiplier. As a result, an electro-clinic effect (b) optically responding to the applied electric field (a) was observed in the $S_A$ phase. The same effect was observed in liquid crystal cells obtained by using other liquid crystal compounds prepared in the foregoing Examples.

EXAMPLE 7

Figure 6:
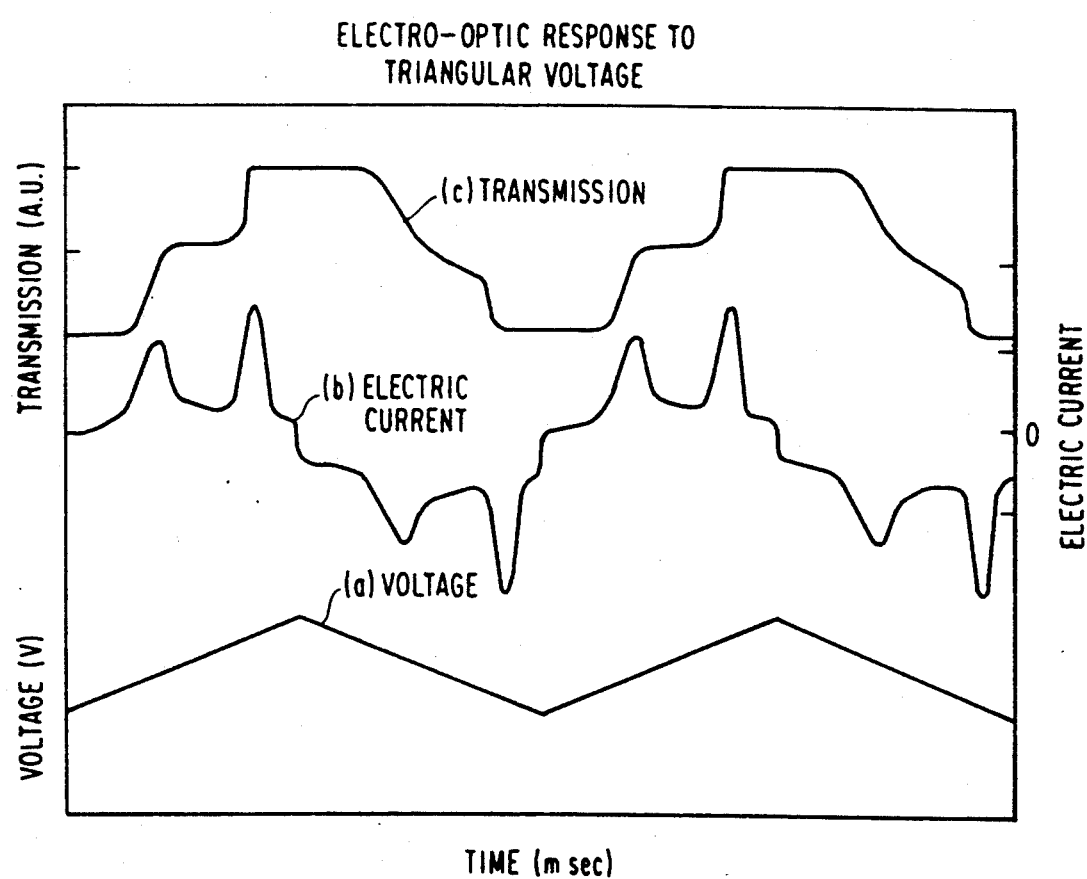
FIG. 6 illustrates switching among the three states of the compound according to the present invention, in which (a) is a triangular voltage wave applied to a liquid crystal electro-optic element, (b) is a polarization inversion current; and (c) is a transmission changing with the voltage (a).

The liquid crystal cell prepared in the same manner as in Example 6 was set in a polarizing microscope equipped with a photomultiplier having a pair of polarizing sheets crosswise in such a manner that the molecular longer axis direction and the polarizer were at an angle of 22.5°. Then, the cell was gradually cooled at a rate of 0.1° to 1.0° C./min until it exhibited an S(3)* phase. The cell was further cooled, and in a temperature range of from 95.0° to 10.0° C., a triangular wave voltage (a) of ±30V and 10 Hz was applied. As shown in FIG. 6, the transmission (c) changed into three states, i.e., a shade state with a minus voltage applied, an intermediate state with a voltage of zero, and a light state with a plus voltage applied; and the polarization inversion current waveform (b) also showed peaks corresponding to these changes. That is, the liquid crystal molecules proved to exhibit three stable states of orientation. The similar effect was observed in liquid crystal cells using other liquid crystal compounds obtained in the foregoing Examples.

As described above, the novel liquid crystal compounds of the present invention exhibit the conventional bistable states or three stable states and can be utilized in a wide range of application, such as display devices and switching devices.

While the invention has been described in detail and with reference to specific embodiments thereof, it will be apparent to one skilled in the art that various changes and modifications can be made therein without departing from the spirit and scope thereof.

What is claimed is:

1. A liquid crystal compound represented by formula (III)

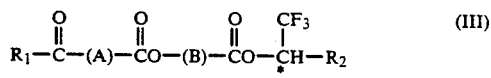

wherein $R_1$ and $R_2$ represents an alkyl group having from 4 to 15 carbon atoms, (A) and (B) each represents a group selected from the group of

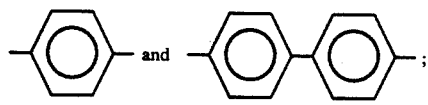

and which compound is in an $S^*_{(3)}$ phase.

2. A liquid crystal compound as claimed in claim 1, wherein $R_1$ is a straight chain alkyl group having from 6 to 12 carbon atoms.

3. A liquid crystal compound as claimed in claim 1, wherein $R_2$ is a straight chain alkyl group having from 5 to 12 carbon atoms.